United States Patent
Noolandi et al.

(10) Patent No.: US 6,800,438 B2
(45) Date of Patent: Oct. 5, 2004

(54) IMAGER FOR DNA SEQUENCER

(75) Inventors: Jaan Noolandi, Mississauga (CA); Robert A. Street, Palo Alto, CA (US); Neville Connell, Alpine, CA (US)

(73) Assignee: Xerox Corporation, Stamford, CT (US)

( * ) Notice: Subject to any disclaimer, the term of this patent is extended or adjusted under 35 U.S.C. 154(b) by 0 days.

(21) Appl. No.: 09/750,560

(22) Filed: Dec. 28, 2000

(65) Prior Publication Data

US 2002/0086293 A1 Jul. 4, 2002

(51) Int. Cl.⁷ .......................... C12Q 1/68; C12P 19/34; C12M 1/34; C07H 21/02; C07H 21/04
(52) U.S. Cl. .......................... 435/6; 435/7.1; 435/91.1; 435/91.2; 435/287.2; 204/155; 702/19; 702/20; 210/656; 210/635; 536/22.1; 536/23.1; 536/24.3; 536/24.31; 536/24.32; 536/24.33
(58) Field of Search ...................... 435/6, 7.1; 204/155; 702/19, 20; 210/656, 635

(56) References Cited

U.S. PATENT DOCUMENTS

| | | | |
|---|---|---|---|
| 4,424,524 A | | 1/1984 | Daniele |
| 4,509,826 A | | 4/1985 | Araghi |
| 4,690,391 A | | 9/1987 | Stoffel et al. |
| 4,712,018 A | | 12/1987 | Stoffel et al. |
| 4,874,492 A | * | 10/1989 | Mackay .................. 204/182.8 |
| 4,927,265 A | | 5/1990 | Brownlee |
| 5,246,866 A | * | 9/1993 | Nasu et al. .................. 436/94 |
| 5,274,240 A | * | 12/1993 | Mathies et al. .......... 250/458.1 |
| 5,627,643 A | * | 5/1997 | Birnbaum et al. .......... 356/344 |
| 5,637,458 A | * | 6/1997 | Frankel et al. .................. 435/6 |
| 5,695,626 A | | 12/1997 | Yeung et al. |
| 5,741,411 A | | 4/1998 | Yeung et al. |
| 5,936,230 A | | 8/1999 | Street |
| 6,136,612 A | * | 10/2000 | Della Ciana et al. ....... 436/546 |

OTHER PUBLICATIONS

Amorphous Silicon Electronics, R.A. Street, Materials Research Society Bulletin, vol. XVII, No. 11, Nov. 1992, pp. 70–76.

Website pages from http://bio.licor.com, (4 pages), (printed Nov. 13, 2000).

Website pages from http://bio.licor.com, (13 pages), (printed Nov. 17, 2000).

* cited by examiner

*Primary Examiner*—Jeffrey Siew
(74) *Attorney, Agent, or Firm*—Fay, Sharpe, Fagan, Minnich & McKee, LLP

(57) ABSTRACT

An improved method for the sequencing of DNA fragments is provided. The method includes using a known process for DNA fragment separation, such as capillary electrophoresis, and imaging the resultant gel plate with a full-width array scanner or a two-dimensional amorphous silicon image sensor array. The DNA sample is placed within a well of the separation apparatus, such as a capillary tube or plurality thereof. The separation apparatus is then placed in a buffer. An electric field is then applied, forming a bias between the ends along which the sample is separated. Once separated, the large area detector scans the entire gel plate and resultant image data is provided. By way of the improved method, the entire gel plate can be scanned at the same time and repeatedly, resulting in greater accuracy and a shorter time to sequence.

23 Claims, 11 Drawing Sheets

IMAGER FOR DNA SEQUENCER

FIELD OF THE INVENTION

The present invention relates to imaging the sequencing of DNA fragments. In particular, the present invention is directed to a DNA sequencing technique using a full-width array scanner or large area detector to selectively image an entire gel sequencing process.

BACKGROUND OF THE INVENTION

In general, modern high-speed DNA sequencers facilitate the migration of DNA fragments attached with fluorescent labels along a gel to achieve separation therebetween. Useful chemical base sequencing information is obtained by the sequences by detecting fluorescence of the fragments at a fixed location. Methods have been developed to most efficiently distinguish the four bases (adenine, thiamine, guanine and cytosine) of interest in DNA sequencing. DNA fragments are identified using a fluorescent dye label for each of the four chemical bases.

Generally, a method known as electrophoresis is used for the above-referenced separation of DNA fragments. Electrophoresis is a separation technique accomplished by inducing the migration of charged molecules (or particles) in an electrolyte under the influence of an electric field. Smaller or more highly charged sample molecules move faster than larger or lower charged molecules. By utilizing this technique, each species of a DNA sample molecule is divided into bands that pass or reach a fixed point at different times. Once these bands pass the fixed point, they are analyzed using a detection method in order to sequence the DNA fragment.

Different types of electrophoresis are used in DNA sequencing. For example, in capillary electrophoresis, a buffer-filled capillary is suspended between two reservoirs of buffer. An electric field is applied to both ends of the capillary to create a bias across the length of the capillary. A sample is introduced at one end of the capillary, typically the capillary end with a higher electric field potential. The sample migrates according to the physical characteristics of the DNA fragments and separate along the electric field bias created.

As a further example, the standard high speed automated DNA sequencers (such as the Applied Biosystems Model 377) make use of a thin gel layer, of several hundred microns, encased between two etched glass plates in order to separate the fluorescent dye labeled DNA fragments by an applied electric field. The separation of the DNA fragments depends on their relative lengths, which can vary by as little as one chemical base. Making use of enzyme chemistry and labeling each of the four bases, by terminating a given DNA fragment with a differently colored dye, the process is accomplished.

Further, in another exemplary technique known as gel electrophoresis, an electrolyte is usually supported by a hydrophilic matrix, the gel, which is coated on a sheet of glass then placed in contact (sandwiched) with another glass plate and finally sealed on each side of the glass plates with a gasket. The samples containing the DNA fragments are applied to the top edge of the gel. The bottom edge of the gel plates is placed vertically in a reservoir containing a buffered electrolyte. A second reservoir is then placed on the top of the glass plates and also filled with a buffered electrolyte. A current is then run to each reservoir by an electrode connected to a power supply. Typically, a gel run will take close to six hours. After the run, the plate is stained in order to visualize the bands of interest.

As is understood, using any of these electrophoresis methods, each fluorescent dye label can be individually detected by a detector. Once a DNA fragment migrates, it is detected by the detector and then the identity of the base is determined based on the fluorescent dye label.

One method that is known to accomplish this determination is a one-color, four-intensity scheme. This scheme is not desirable, however, in controlling the polymerase and in maximizing the signal-to-noise ratio. A two-color, two-intensity method has also been developed which has advantages over the one-color scheme. These advantages include simpler optical arrangement, good light collection and a straightforward algorithm. However, the two-color method still has disadvantages in controlling the polymerase. Thus, the most commonly used technology is a four-color method that uses four standard dyes for each of the chemical bases of DNA.

In addition, as expressed above, to effectively sequence the DNA fragments that are placed within the separation apparatus, a suitable detection system is necessary. Conventionally, a detector is positioned at the end of the migration lanes. The detector then detects each DNA fragment as it migrates to the end, thereby sequencing the DNA fragments. A common disadvantage of all known detection techniques, however, is that they consume an excessive amount of time.

For example, in the case of detection of a capillary electrophoresis system, the light is collected from the end of the capillary tube where the DNA fragments migrate. Detection is accomplished by putting a lens in front of the fixed point and a detector behind the lens. The detector collects all of the light that was emitted through the lens. However, in this system, not all of the light is collected and detected, which poses a particular problem if the size of the emission is large. Moreover, the time required to accurately detect in this fixed end detector is excessive.

Another older technology used the separation of radioactive isotope labeled DNA fragments followed by overnight exposure to special film. This technology showed that over 300 bases were present in the entire gel after high field electrophoresis lasting seventeen minutes. However, this process of detection is also excessively time consuming.

Other devices use a single photomultiplier tube (PMT) imager scanned across the plate, or a charge-coupled device (CCD) to image a line. In both situations, the time necessary for imaging is excessive. In the case of a CCD, the detector is optically coupled to the capillary array by way of the capillaries in the array being optically coupled to the linearly aligned pixels. A sample containing a fluorescent target species, such as a DNA fragment, is introduced into the intake end of the optically coupled capillary such that it migrates through the capillary toward the outflow end. Fluorescence emission from the target species is then induced by irradiating it with a beam of coherent light. Fluorescence emission is detected by the image array detector through the transparent portion of the optically coupled capillary using the optically coupled pixels.

The detection systems of the prior techniques pose many problems in the efficiency of DNA sequencing and imaging. The prior systems are very slow. For example, some fixed end detection systems require up to eight hours in order to detect one sample. Further, by using a prior art detector, all of the possible data is not collected. For example, the relationship between the DNA fragments cannot be recorded as they migrate from one end of the separation apparatus to the other end. Another reason that the prior art detection systems are not efficient is that these systems typically only detect one band at a time, e.g. the band that has reached the end of the separation apparatus in fixed end detection. This provides no information about where other bands have migrated with respect to the bands that are being detected.

The present invention overcomes the above-referenced problems and others and provides an improved method for the imaging of DNA fragments for DNA sequencing.

SUMMARY OF THE INVENTION

The present invention provides a technique for sequencing an entire sequencing plate or separation apparatus holding DNA fragments using known methods of DNA sequencing in combination with a scanner or large area detector. The resultant system and method improve speed of detection and processing and more accurately achieve sequencing of DNA fragments.

In one aspect of the invention, the method comprises steps of placing a DNA sample within a buffer in separation apparatus, applying an electric field across the separation apparatus to create a bias in the buffer such that the DNA sample migrates from one end of the apparatus to another end along a migration channel, separating the DNA sample into fragments along the migration channel within the buffer, detecting fluorescent light emitted from the fragments along the migration channel and generating a full image of the separation apparatus and the separated DNA fragments based on the detecting.

In another aspect of the invention, the apparatus comprises a separation apparatus operative to receive a DNA sample and facilitate migration and separation into fragments of the DNA sample along a migration channel within the apparatus, a detector operative to detect light emitted the DNA fragments along the migration channels and an image processor operative to generate image data representing a full image of the separation apparatus and the fragments.

In another aspect of the invention, the detector is a full width linear scanner.

In another aspect of the invention, the detector is an amorphous silicon array.

One advantage of the present invention is to speed up DNA sequencing by fluorescence labeling using scanning and/or large area detection.

Another advantage of the present invention is to use multiple scans of the capillary electrophoresis gel to calculate an optimum combination of electrophoresis and two-dimensional imaging steps to speed up the sequencing process.

Yet another advantage of the present invention is that many different plates may be monitored at the same time, as the scanner may scan an entire plate in a short time.

Yet another advantage of the present invention is that the optical efficiency of the lens system employed is much more efficient by having greater light collection.

DRAWINGS OF THE INVENTION

The invention may take physical form in certain parts and arrangement of parts, the preferred embodiments of which will be described in detail in the specification and illustrated in the accompanying drawings, which form a part hereof and wherein.

DETAILED DESCRIPTION OF THE INVENTION

In the present invention, a scanner or large area detector is employed to image the sequence of DNA fragments that are being separated by way of electrophoresis. Electcophoresis employed may be of any of the types discussed above or others including capillary electrophoresis, gel electrophoresis, etc.

As noted above, in the typical electrophoresis process, the DNA sample is placed at the end of a migration channel of a sequencing plate. The entry end of the plate is at a higher potential than the opposite end as a result of the applied electric field. The DNA fragments within the sample separate and migrate to the opposite end of the migration channel of lower potential according to the size of the particular DNA base fragment. The lightest base fragments will travel more quickly than the larger base fragments. Once the DNA fragments have separated, it is desirable to image the results so that the individual DNA fragments, which separate chemical bases, can be sequenced.

According to the present invention, imaging of the entire sequencing plate is preferably accomplished using a full-width array scanner or an amorphous silicon array. Use of such imaging techniques has significant advantages over the prior art systems inasmuch as they result in a significant gain in sequencing time. That is, the system of the present invention reduces the amount of time required to obtain useful data to analyze electrophoresis processes. The time required to detect the light being emitted from the samples and process the resultant data does not significantly differ from the time required to scan and process other image data, such as that obtained in document reproduction and rendering applications. As such, not only is the time required for a particular detection process reduced, but more detection processes can be had with respect to any one DNA sequencing event. This, of course, provides useful temporal data on the electrophoresis. Further, the data collected is of a nature that inherently includes more information than is obtained in present or old systems. In this regard, the data represents an image of the entire sequencing plate as opposed to only a limited portion of the plate or sequencing medium. Moreover, because data is collected from the entire plate, relationships between the progress of different fragments can be considered in any analysis of the electrophoresis process. The resultant data can be used or manipulated in any suitable manner that comports with the intent and/or objectives of the test administrator and/or the system designer.

Figure 1:
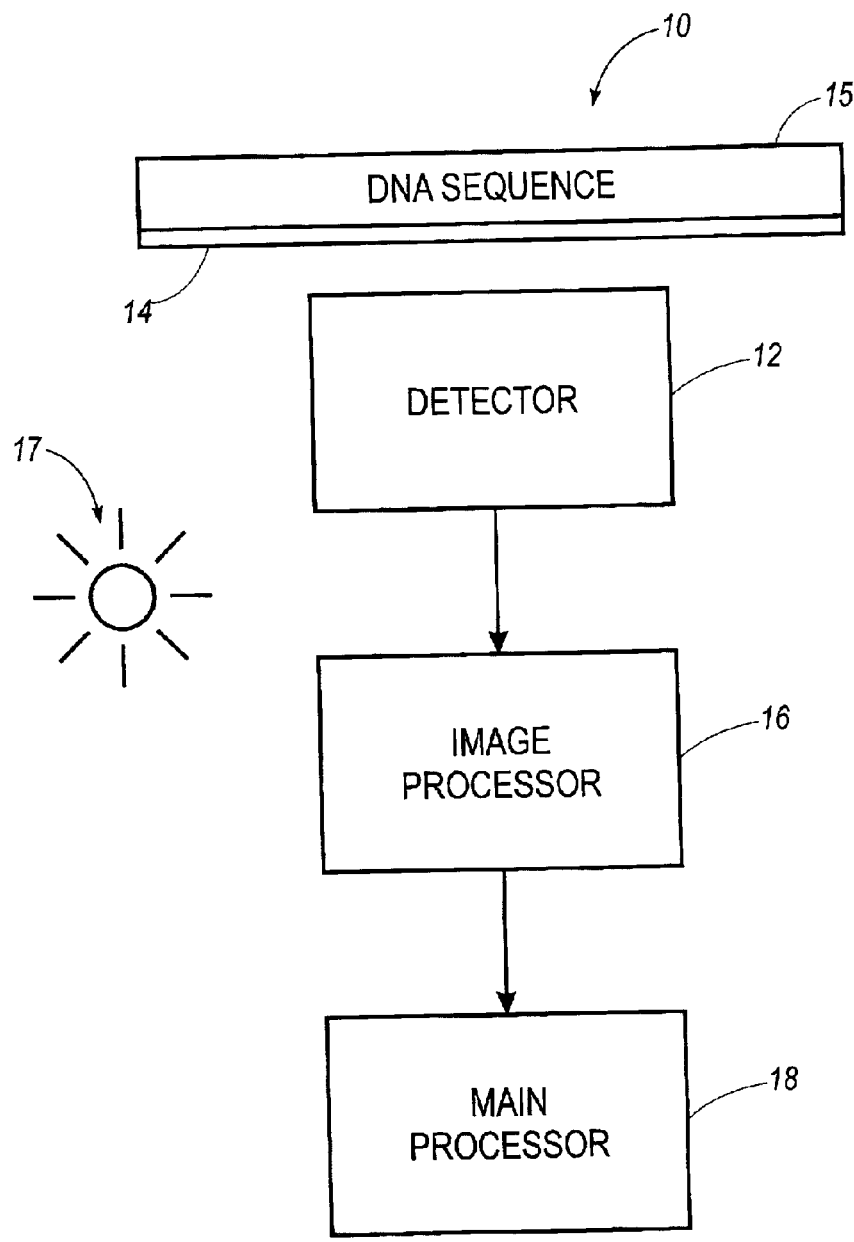
FIG. 1 is an overall block diagram representing the system for the present invention.

With reference now to the drawings wherein the showings (which generally only representatively show the elements) are for purposes of illustrating the features of the invention and not for purposes of limiting same, FIG. 1 shows a system 10 according to the present invention for imaging a DNA sequence. In operation, the method according to the present invention provides that a detector 12 detects the emission of light from a DNA sample or sequence 14 disposed on a separation apparatus comprising a sequencing plate 15 wherein the DNA fragments are separated in the buffer which may be, for example, a gel or polymer solution. Significantly, a detector 12 scans the entire plate 15 at predetermined points in time to obtain the necessary data to accomplish the objectives of the present invent ion. The data collected by the detector—which represents an image of the entire sequencing plate at a given time—is then processed by an image processor 16. Based on the resultant processed data provided by the image processor 16, the sequence of the DNA fragments within the DNA sample is determined by a main processor 18 using known techniques. Of course, the plate 15 is also provided with a source to produce a suitable electric field as those of skill in the art will appreciate.

Also shown in FIG. 1 is an illumination source 17, which preferably takes the form of a laser, e.g. an argon laser, illuminating across the plate in a direction perpendicular to the direction of fragment migration. The illumination could also occur in a direction parallel to the migration. In one embodiment, the argon laser moves with the scanner. An alternate configuration uses a light bar of blue gallium nitride light emitting diodes focused onto the plate by an appropriate lens system such as a SELFOC lens system, which is a trade-name of Nippon Sheet Glass Co. of Japan. A SELFOC lens consists of graded-index fiber rods with a parabolic index profile, which are suitable for use as cylindrical microlenses. In addition, a laser light illumination source could be disposed on an edge of a detector bar and a linear array detector could be disposed on an opposite edge, or rear, of the detector bar. As still a further alternative, when implementing the invention in connection with the capillary electrophoresis sequencing technique, the capillaries could be illuminated from their ends, using internal reflection to propagate the laser light up the entire length of the capillary to get the maximum excitation intensity of the fluorescent dyes attached to the DNA fragments. This improves the efficiency of the system in that very little unused light is generated.

It should be understood that the processes associated with DNA sequencing, although generally described herein, are well known in the field such as described in U.S. Pat. No. 4,927,265 and hereby incorporated by reference. Moreover, the image processing and other data processing that is accomplished according to the present invention is based on imaging and processing technology that is well known in the art. For example, the techniques of scanning an object to obtain rasterized data that can then be processed as image data are well known and may be readily implemented to achieve the objectives of the present invention. In this regard, various hardware and software techniques could be implemented to that end, as those skilled in the art will appreciate upon a reading of the present application.

Likewise, the optical processes and systems implemented according to the present invention are of a type that should be apparent to those skilled in the art upon a reading of the present disclosure. For example, the lens systems implemented have operational characteristics that are well known. In addition, the optical filters may be those conventional filters that are presently available in the optical field that would satisfy the objectives of the present invention.

Figure 2:
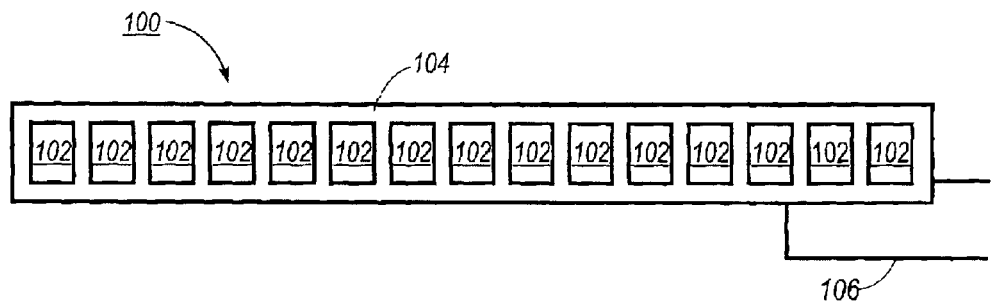
FIG. 2 shows a typical example of a linear detector array from an underside elevation.

As to the processes associated with detection, it is to be appreciated that either the full width array scanner or the amorphous silicon array can be used as the detector 12 to achieve the advantages of the invention. In this regard, a full-width linear detector array 100 employed in the present invention is shown in FIG. 2 and is comprised of a plurality of scanning array sensor elements 102 that are assembled on a base member or bar 104. The sensor elements 102 are aligned in an end to end relation to form a composite scanning array or chip. The detector array 100 generally includes a rectangular base or bar (which is normally silicon) 104, with a plurality of sensors 102 arranged in a linear row or array on one surface. The sensor rows are generally parallel to the side edge of the array base. Operation of the sensors can be controlled by cooperating control circuitry, such as logic gates and a shift register, which is measured through the use of a data readout 106. To permit an array to be abutted to other like arrays, if desired, the row of sensors extends to the end of the array base.

Full width sensor arrays of this type are used in document scanners. For example, arrays with 600 spot per inch resolution (42 micron pixel pitch) and a total length of at least 12 inches are known. Such arrays sense color images using three adjacent rows of sensors with suitable color filters. The array is fabricated with a crystalline silicon CMOS process and electronics for the readout is fabricated in the same silicon integrated circuit. The full width array is assembled by abutting several individual integrated circuits, which can be positioned with an accuracy of about one to two microns.

The use of different detectors allows the implementation of a varying range of wavelengths. The full width array uses crystalline silicon and is sensitive from about 400 to about 900 nanometers, while the amorphous silicon arrays (described in more detail below) are sensitive from about 400 to about 700 nanometers. Both of these types of detectors span a range that is wide enough to detect the fluorescence emission.

Figure 3:
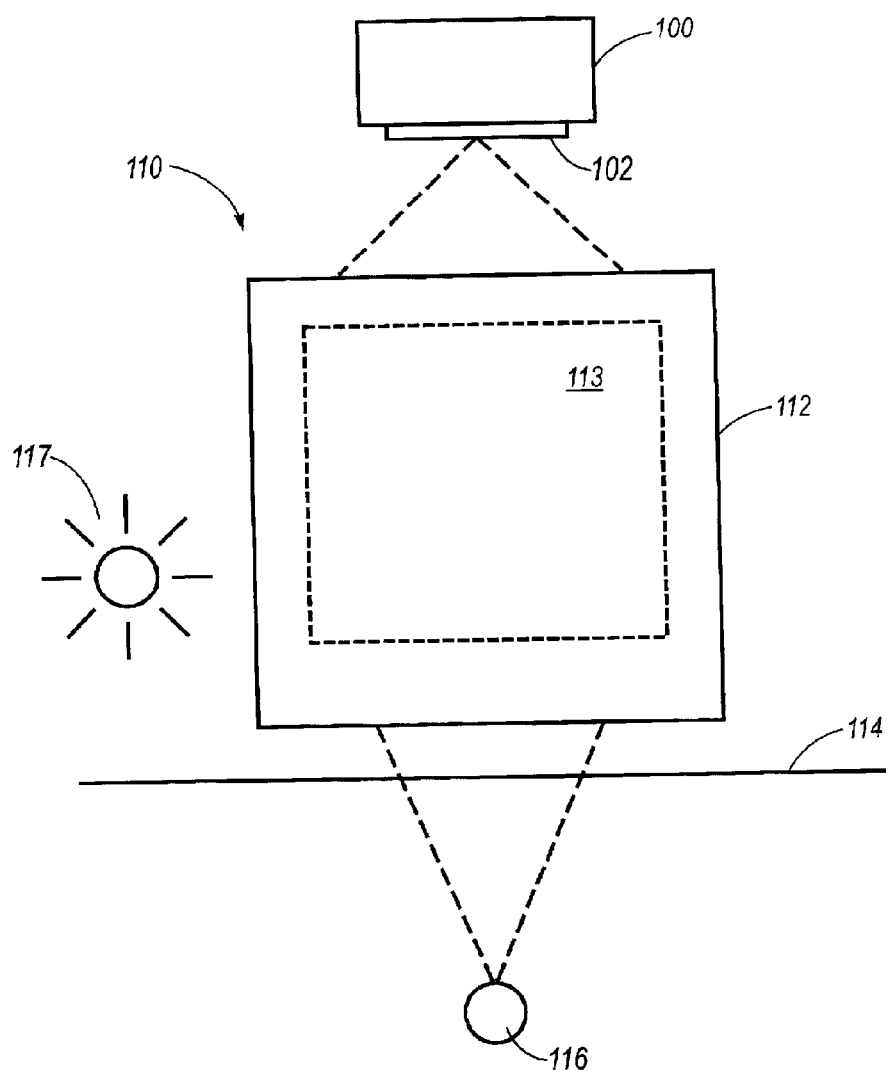
FIG. 3 shows a side view a linear detector system according to the present invention.

With reference to FIG. 3, a linear detector system according to the present invention is shown. The linear detector system 110 comprises linear detector array 100 (identical in configuration to the linear array illustrated in FIG. 2) at the focus of a lens system 112 and an optical filter 114. As illustrated, the lens 112 is preferably a SELFOC lens including a plurality of cylindrical lens elements 113, although any suitable lens system could be implemented to accomplish the objectives of the invention. The optical filter 114 may take any suitable form that accomplishes the objectives of the invention.

In order to image an object 116, the object 116 is illuminated by an illumination source 117 (only representatively shown in the figures), which generates a fluorescent emission from the object. As noted above, the illumination source according to the present invention is preferably a laser illumination source, although various other illumination sources would suffice. This fluorescent emission is then detected by the detector array 100. In one embodiment power of the illumination source is in the range of about 10 to about 100 milliwatts. Indeed, an argon ion laser known to be used in prior DNA sequencers (e.g. ABI 377 system) operates in the range of 20–40 milliwatts.

Figure 4:
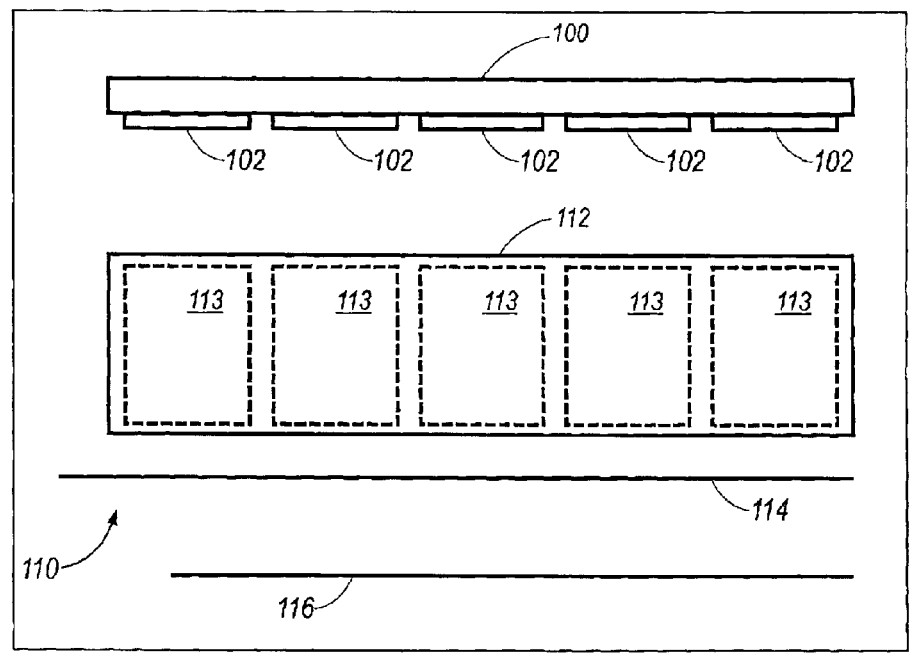
FIG. 4 shows a front view of the device illustrated in FIG. 3.

Another view of the linear detector system of FIG. 3 is shown in FIG. 4. In this view, an advantage of the SELFOC lens system is illustrated. In this regard, the lens elements 113 of the lens system are aligned with the sensor elements 102 of the linear array 100. This results in improved detection and processing capabilities.

Figure 5A:
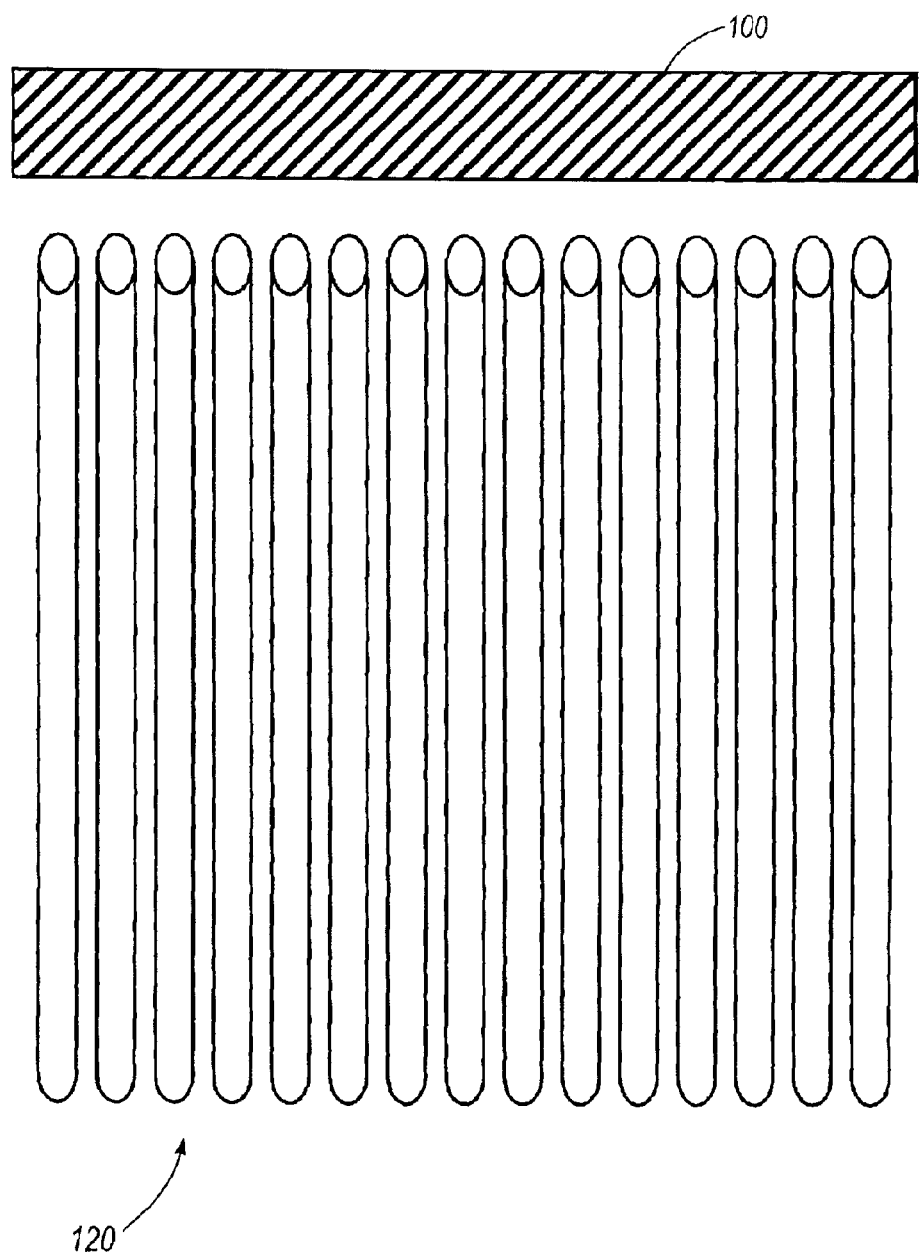
FIG. 5a shows a system of the present invention using a linear scanning array to image capillary electrophoresis parallel to the electric filed for migration.

This system may be implemented using any of the electrophoresis techniques described herein and others. With respect to capillary electrophoresis, as discussed above and as now more particularly shown in FIG. 5a, a plurality of capillary tubes 120 are used to separate DNA fragments. The two ends of the capillary tubes are placed in a buffer, and the same buffer fills the interior of the capillary tube. In one existing system, ninety-six (96) capillary tubes are disposed along a sequencing plate. An electric field is applied across the tubes, thereby creating an electrical field bias from one end of the plate to the other end. As such, one end of the capillary tube has a higher potential than the other end, which results in a bias from one end (from the higher potential) to the other end of the capillary tube (to the end with a lower potential).

As shown, the array 100 of the system 110 (not shown in its entirety) is positioned to move and scan in a direction that is parallel to the length of the capillary tubes to collect data that will be useful to image the entire sequencing plate. More particularly, the linear array 100 initiates a scanning process at the end of the capillary where the sample is placed within a well, i.e., the end with a higher potential. Thus, as the sample migrates through the capillary and separates, the linear detector will scan in the direction of the sample along the entire sequencing plate in order to receive data of the sample separation as or once it separates. Of course, it is to be appreciated that such a scanning may be initiated at a convenient time to be determined by the administrator of the sequencing process in order to obtain data at the most opportune instances. Alternatively, scanning may be initiated at a plurality of different times during the sequencing process. In this manner, a plurality of images may be analyzed in order to obtain useful data on the relative separation rates for all of the substances.

As noted above in connection with FIG. 1, once the plate is scanned, the scan data, e.g. rasterized data, is provided to an image processor 16 wherein appropriate image data is generated for analysis purposes. This image data is then provided to a main processor 18 so that appropriate sequencing analysis operations may be performed.

Figure 5B:
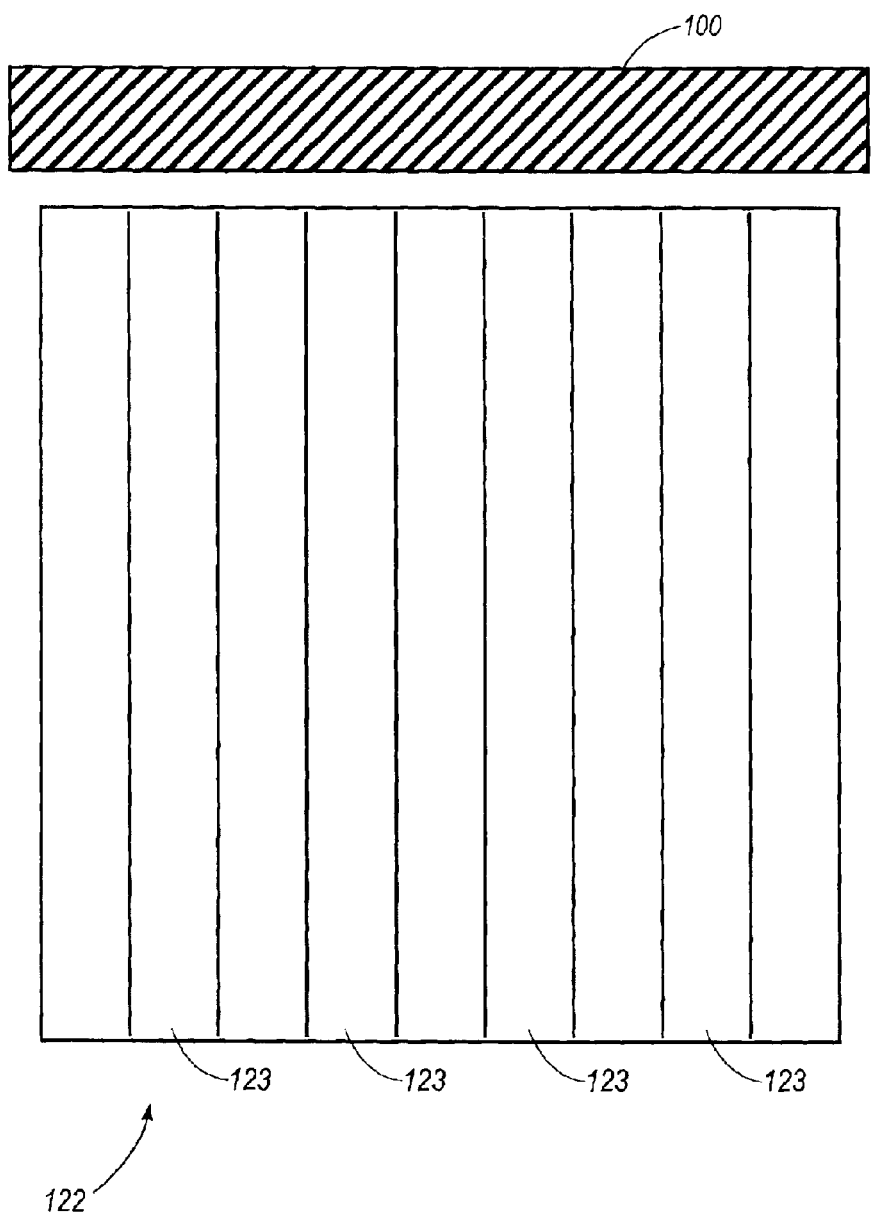
FIG. 5b shows a system of the present invention using a linear scanning array to image lithographically etched plate electrophoresis parallel to the electric filed for migration.
Figure 5C:
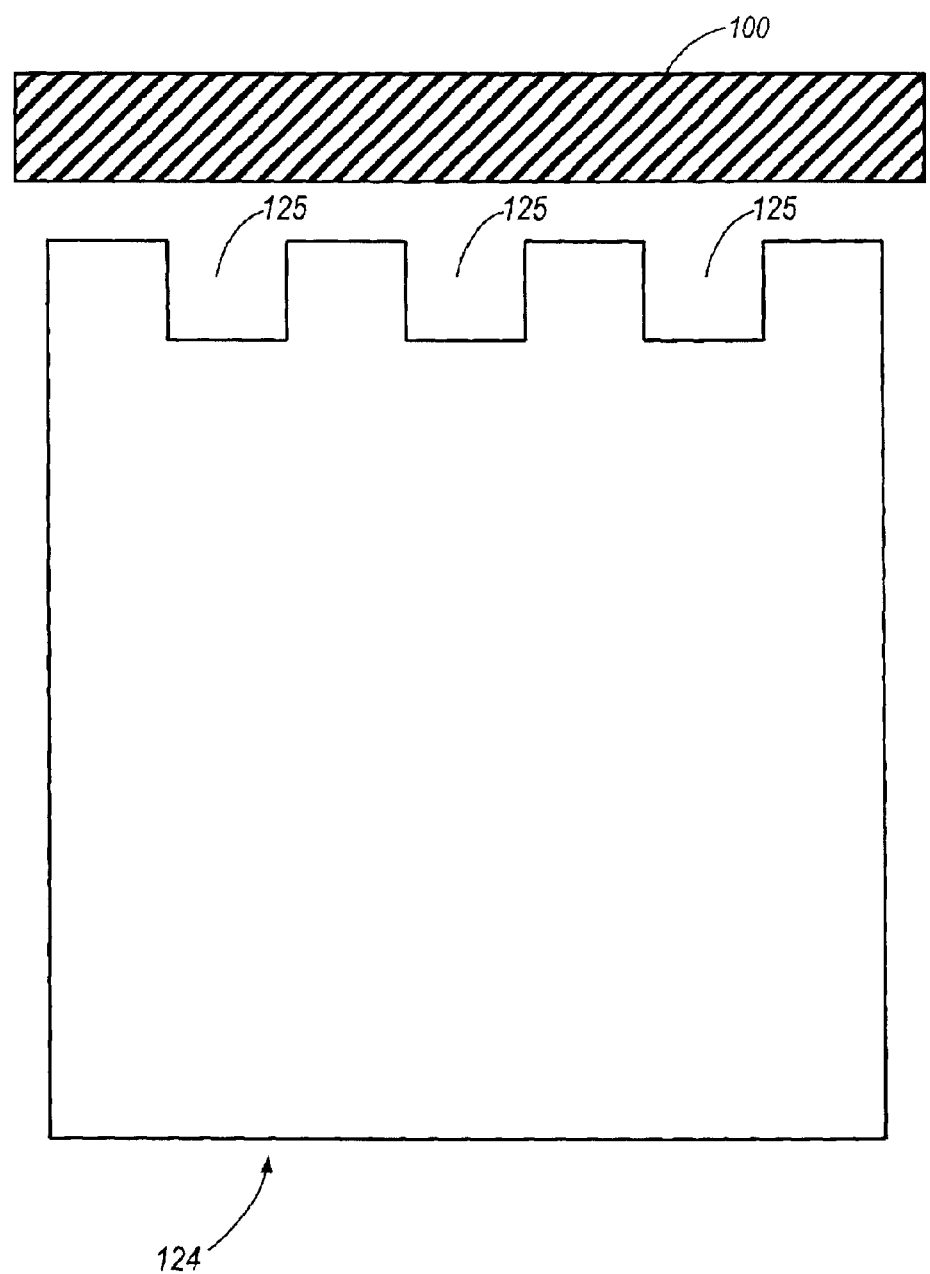
FIG. 5c shows a system of the present invention using a linear scanning array to image gel electrophoresis parallel to the electric filed for migration.

Other separation schemes, such as using glass plates, see FIG. 5b, with lithographically etched channels or using gel electrophoresis, see FIG. 5c, could also be used. Preferably, like the embodiment shown in FIG. 5a, the linear detector array 100 will scan parallel to the direction of the bias formed in the separation apparatus. Moreover, the data obtained will be processed as described above.

In FIG. 5b, for example, the array 100 is positioned to scan the sequencing plate 122 in the direction that is parallel to the length of the channels 123, of which a plurality is provided on the plate. As noted above, the plate is preferably formed of a glass material. Moreover, the channels are etched into the glass material using known techniques and may be provided on a single substrate of glass in such manner so as to be mated with a glass cover having no etched channels. Alternatively, the channels may be partially etched in two separate substrates of glass, the mating of which forms the full channels.

In FIG. 5c, the array 100 is disposed so that it scans the plate 124 in the direction in which the DNA fragments migrate. In this regard, it should be appreciated that the DNA sample is placed in the system in the ports 125 formed in the entry end of the plates that maintain the gel. As those skilled in the art will appreciate, these ports facilitate the orderly migration of fragments through the gel.

Figure 6A:
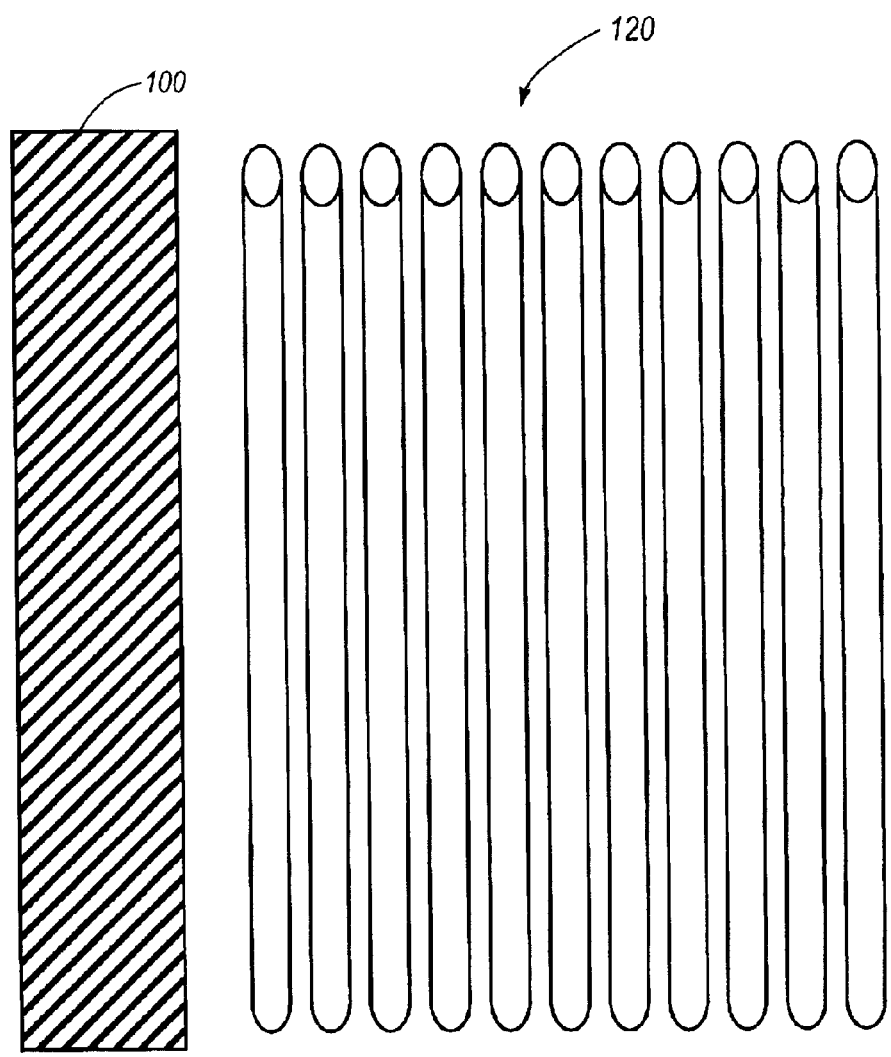
FIG. 6a shows a system of the present invention using a linear scanning array to image capillary electrophoresis perpendicular to the electric filed for migration.
Figure 6B:
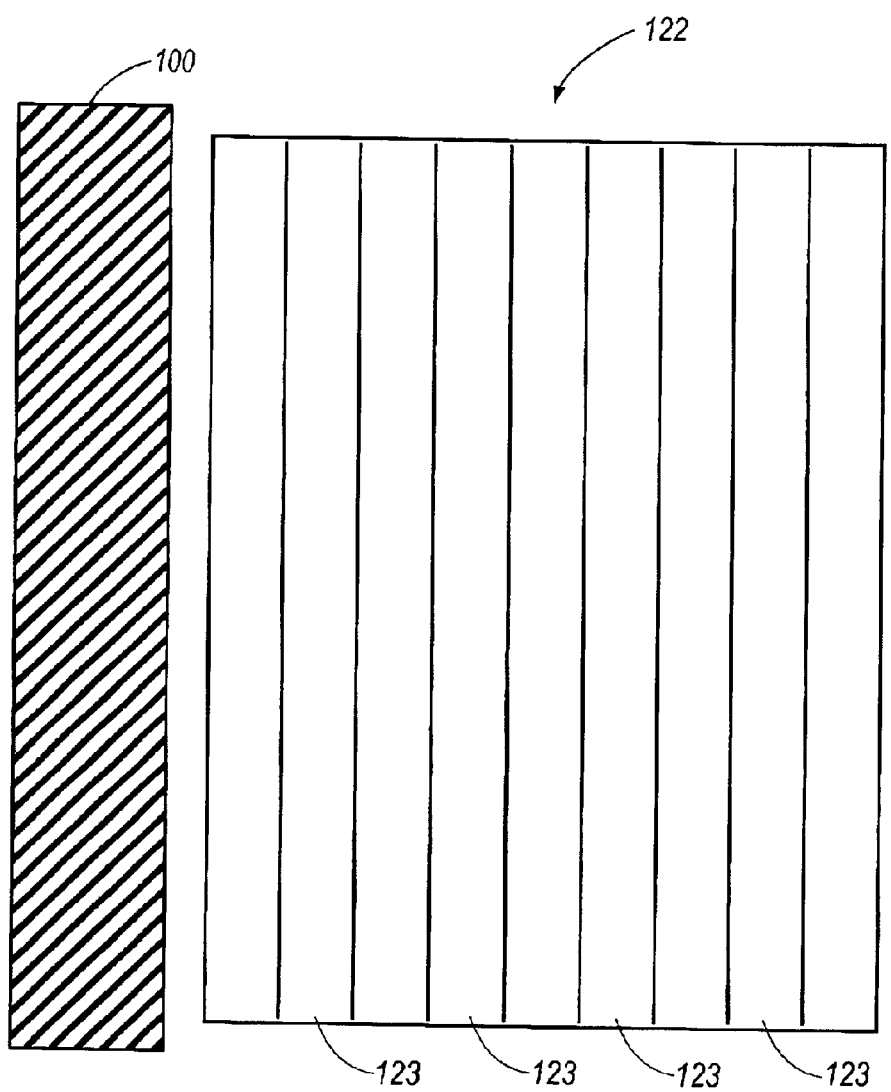
FIG. 6b shows a system of the present invention using a linear scanning array to image lithographically etched plate electrophoresis perpendicular to the electric filed for migration.
Figure 6C:
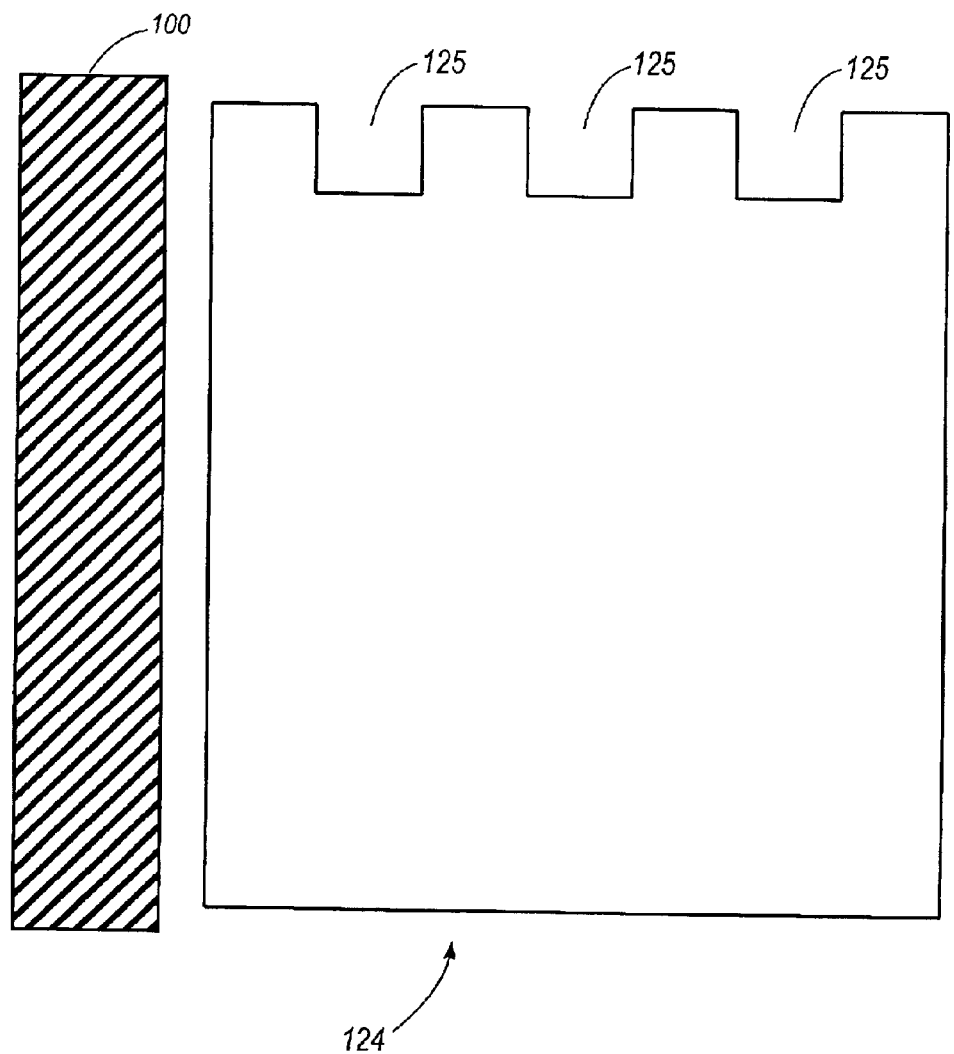
FIG. 6c shows a system of the present invention using a linear scanning array to image gel electrophoresis perpendicular to the electric filed for migration.

Another method of linear array scanning would be to scan the separation apparatus used in the sequencing technique in a direction that is perpendicular to the direction of the electric field that is created or perpendicular to the direction of migration of the sample fragments. In this regard, FIG. 6a represents the use of perpendicular movement of a linear scanning array 100 relative to the plurality of capillary tubes 120 to image DNA fragments using capillary electrophoresis. FIG. 6b represents the use of perpendicular movement of a linear scanning array 100 relative to the channels 123 of etched plate(s) 122 to image DNA fragments using lithographically etched glass plates. FIG. 6c represents the use of perpendicular movement of a linear scanning array 100 relative to a sequencing plate 124 to image DNA fragments using gel electrophoresis as the method of separation.

It should be appreciated that, in one embodiment, a single pass of the scanner is used to collect the data that is ultimately used to produce the processed image. However, if the linear array is not of sufficient length to scan and collect data for the entire plate in a single pass, then multiple passes are used. In these cases, appropriate scanning and imaging techniques should be employed to accommodate the multiple passes to create a single image. Accommodations would also be made to account for any time differential between passes.

In another embodiment of the invention, the linear scanning array is stationary while the separation apparatus is moved to allow detection. It is to be appreciated that this alternative can be used in both perpendicular and parallel scanning. However, it is preferred that the embodiments described in connection with FIGS. 5a–6c be implemented due to the apparent advantages of maintaining the sequencing plate in a fixed position while making use of the relatively advanced and well developed art of image scanning.

Figure 7:
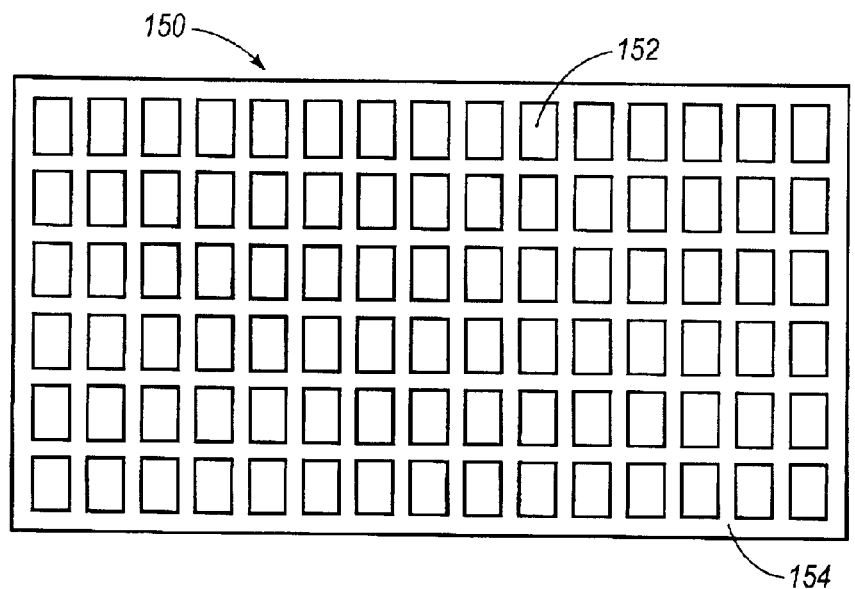
FIG. 7 shows a two-dimensional array scanner.

Alternatively, as shown in FIG. 7, a large area two-dimensional amorphous silicon image sensor array 150 may be used to obtain an image of the gel plate. As shown, the array 150 is comprised of a plurality of sensor elements, one of which is represented at 152, positioned on a substrate 154. The elements are arranged in rows and columns. Preferably, the array is of a size to match or exceed the size of an electrophoresis plate that is used in a DNA sequencing and includes a sufficient number of suitably arranged sensor elements to generate an image that can be processed and used for analysis of the electrophoresis process.

Amorphous silicon arrays are well known for real time imaging of incident high energy radiation, since they provide a relatively large size image sensor array. Sensor arrays operate on the principal of integrating a charge representative of the quantities of visible light incident on the sensor.

Light creates electron hole pairs in the sensor and an applied voltage separates the electrons and holes to provide the charge on the sensor. In some cases, a phosphor converter generates the visible light from incident high-energy radiation but this is not necessary for the present application. In preferred arrangements, the array is sensitive at the required wavelengths.

In the applications of amorphous silicon two-dimensional arrays, the sensor array that is collecting the visible light is made up of a plurality of individual pixels, e.g. elements 152, which collectively represent the image generated by the imager. Each pixel typically contains an individual light sensor, a transistor that functions as a switch to communicate a signal representative of the sensed light, and various metallization lines that allow the representative image to be read out to an external device. The light sensor first accumulates a charge representative of the amount of visible light incident upon it and then applies a pulse to a gate line that turns on all the gates of those sensors in a column to which the particular pulse gate is attached. The pulse causes the charge on the sensors to be transferred to the data lines for that column of sensors. That output essentially resets the sensor in the column back to zero so that the sensor may begin collecting charge again.

Figure 8:
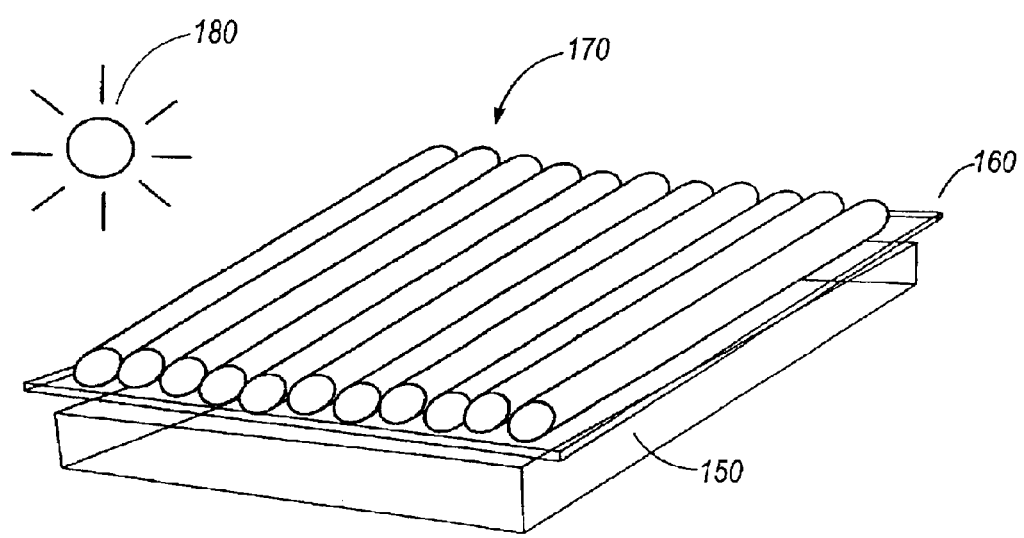
FIG. 8 shows a system of the present invention using a two-dimensional array scanner.

Referring now to FIG. 8, an implementation of the amorphous silicon array 150 is shown. More specifically, the array 150 is positioned directly beneath an optical filter 160 that is positioned in near proximity to the sequencing plate 170. As shown, the sequencing plate is of the type including capillaries to accomplish capillary electrophoresis. However, any of the sequencing plates known and/or discussed herein may be used. Also shown is a light source 180, preferably of a laser type or an LED array arrangement. The light source preferably illuminates the entire plate but could also be scanned across the plate. As will be appreciated, in operation, the light source illuminates the sequencing plate with appropriate laser light and the DNA fragments carried by the plate are fluoresced. Subsequently, the amorphous silicon array detects the emitted light after such light is filtered. Although not shown in the figure, the data collected by the detector is processed and appropriate analyses are conducted by the system.

Figure 9:
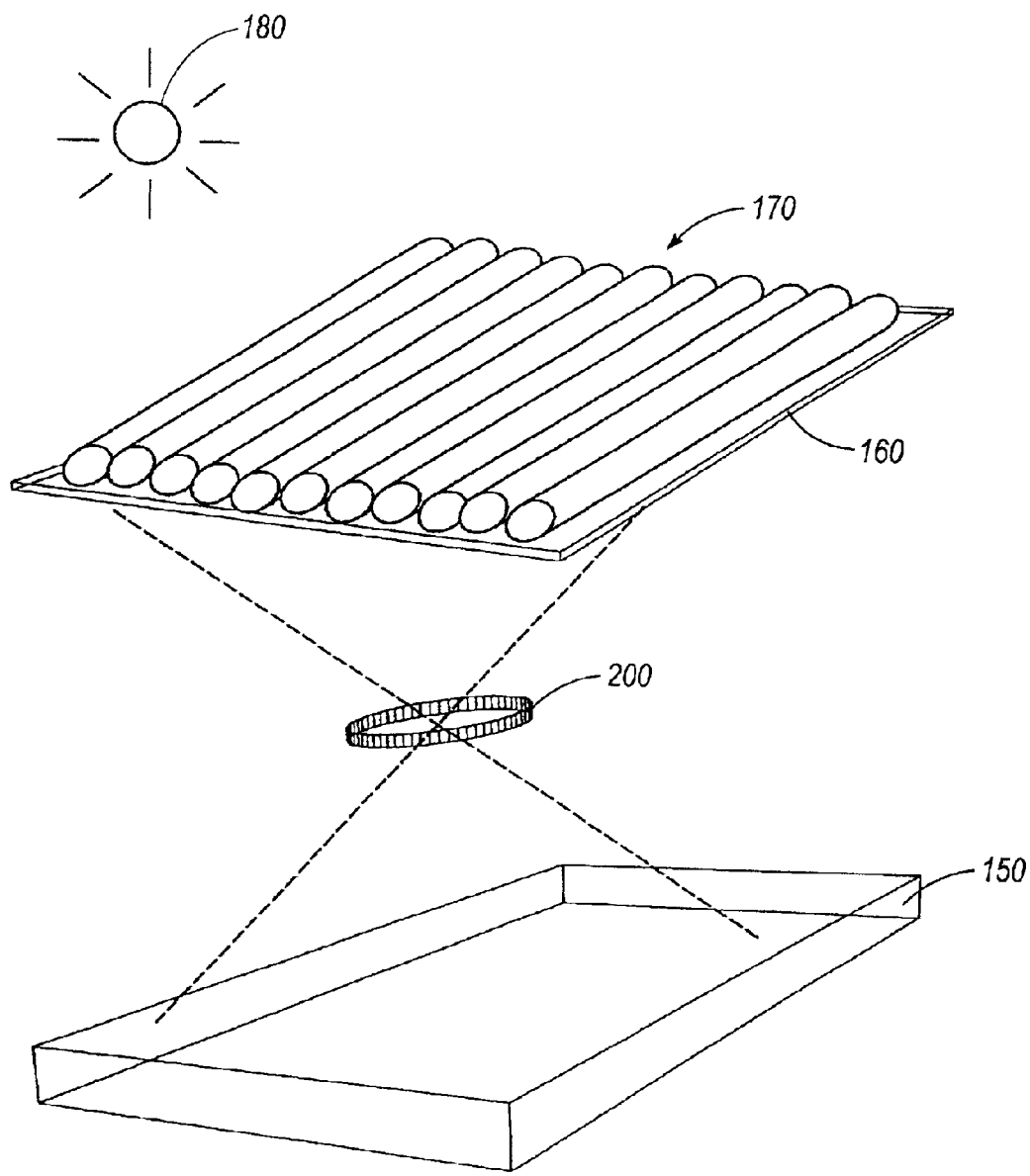
FIG. 9 shows another system of the present invention using a two-dimensional array scanner.

An alternative embodiment of the invention incorporating use of the amorphous silicon array is representatively illustrated in FIG. 9. More particularly, the array 150 is shown in spaced relation to the filter 160 and the sequencing plate 170. However, a focussing lens 200 is disposed between the filter and the array. The purpose of the lens is to focus light emitted by the sample fragments onto the array so that a suitable image may be obtained. The use of the lens is, of course, advantageous in circumstances where the filter and plate cannot be brought in close proximity to the array. Those skilled in the art will further appreciate that there are circumstances where the use of the lens is otherwise desired as well.

Whether a scanner or amorphous silicon array is used, a full plate imaging device preferably will have the required spatial resolution, sensitivity and spectrum filtering ability to be able to separate the four individual emission bands of the fluorescent labeled DNA fragments. The spatial resolution of both the full width array scanners and the amorphous silicon imagers is more than sufficient for the present electrophoresis plates or the capillary structures and can provide imaging coverage for at least 75% of the plate. Separation of the different emission spectra can be performed with color filters on the scanners. For the full width array, a preferred arrangement is to provide four arrays with separate color filters optimized for each of the emission bands. The two-dimensional amorphous silicon array can be coated with a matrix of color filters as used in the a-Si:H liquid c.rystal display technology.

The scanner sensitivity is important since the emission from the gel is difficult to detect. When scanning the whole plate, the scan time is much shorter. The full width scanner or two-dimensional array not only has a shorter scan time, but also has a better light collection. The optical efficiency of a lens system is given by, Efficiency=$1/[1+8f^2(1+m)^{-1}]$, Where f is the f-number and m is the magnification (defined as object full width array has about ten times the light throughput as compared to the prior art CCD, which is due to of the difference in the value of the magnification. This increased sensitivity allows a faster scan time for the full-width array as compared to a prior art CCD apparatus. The two-dimensional array has a larger sensitivity because it images multiple lines simultaneously, thus a two-dimensional array efficiency is much higher. The present invention thus provides a more efficient method for detection of the DNA fragments.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

What is claimed:

1. A method of sequencing DNA fragments comprising:
   placing a DNA sample within a buffer in separation apparatus having a plurality of migration channels;
   applying an electric field across the separation apparatus to create a bias in the buffer such that the DNA sample migrates from one end of the apparatus to another end along a migration channel;
   separating the DNA sample into fragments along the migration channel within the buffer;
   detecting fluorescent light emitted from the fragments along the migration channel using a full-width array scanner capable of scanning an entire width of the separation apparatus simultaneously; and,
   generating a full image of the separation apparatus and the separated DNA fragments in a single scan pass.

2. The method of claim 1 wherein the buffer is a gel.

3. The method of claim 1 wherein the buffer is a polymer solution.

4. The method of claim 1 wherein the separation apparatus comprises a plurality of capillary tube forming the migration channels.

5. The method of claim 1 wherein the separation apparatus comprises a set of glass plates with lithographically etched channels forming the migration channels.

6. The method of sequencing DNA fragments comprises:
   placing a DNA sample within a buffer in a separation apparatus having a plurality of migration channels;
   applying an electric field across the separation apparatus to create a bias in the buffer such that the DNA sample migrates from one end of the apparatus to another end along a migration channel;
   separating the DNA sample into fragments along the migration channel within the buffer;
   detecting fluorescent light emitted from the fragments along the migration channel using an amorphous silicon two-dimensional image sensor array and, generating a full image of the separation apparatus and the separated DNA fragments.

7. The method of claim 1 wherein the detecting comprises detecting at a first time and then repeating the detecting after DNA fragments migrate through the gel for an additional period of time.

8. An apparatus for the sequencing of DNA comprising:
a separation apparatus having a plurality of migration channels operative to receive a DNA sample and facilitate migration and separation into fragments of the DNA sample along a migration channel within the apparatus;
a detector operative to detect light emitted from DNA fragments along the migration channels wherein said detector comprises a full-width array scanner capable of scanning an entire width of the separation apparatus simultaneously; and
an image processor operative to generate image data representing a full image of the separation apparatus and the DNA fragments in a single scan pass.

9. The apparatus of claim 8 wherein the separation apparatus comprises:
a plurality of capillary tubes comprising the migration channels;
a buffer; and,
a means for providing an electric field to create a bias between ends of the capillary tubes.

10. The apparatus of claim 8 wherein the separation apparatus comprises:
a stacked pair of lithographically etched glass plates;
a buffer; and,
a means for providing an electric field to create a bias between ends of the glass plates.

11. The apparatus for the sequencing of DNA comprising:
a separation apparatus having a plurality of migration channels operative to receive a DNA sample and facilitate migration and separation into fragments of the DNA sample along a migration channel within the apparatus;
a two-dimensional amorphous silicon image sensor array detector operative to detect light emitted from DNA fragments along the migration channels; and,
an image processor operative to generate image data representing a full image of the separation apparatus and the DNA fragments.

12. A system for sequencing DNA fragments comprising:
means for placing a DNA sample within a buffer in a separation apparatus having a plurality of migration channels;
means for applying an electric field across the separation apparatus to create a bias in the buffer such that the DNA sample migrates from one end of the apparatus to another end along a migration channel;
means for separating the DNA sample into fragments along the migration channel within the buffer;
means for illuminating the DNA fragments;

an amorphous silicon two-dimensional image sensor array for detecting fluorescent light emitted from the illumination fragments along the migration channel; and,
means for generating a full image of the separation apparatus and the separated DNA fragments.

13. The system of claim 12 wherein the illumination means comprises a laser that illuminates perpendicular to the direction of migration of the DNA fragments.

14. The system of claim 12 wherein the illumination means comprises a laser that illuminates along the direction of migration of the DNA fragments.

15. The system of claim 12 wherein the illumination means comprises a light emitting diode bar.

16. A system for sequencing DNA fragments comprising:
means for placing a DNA sample within a buffer in a separation apparatus having a plurality of migration channels;
means for applying an electric field across the separation apparatus to create a bias in the buffer such that the DNA sample migrates from one end of the apparatus to another end along a migration channel;
means for separating the DNA sample into fragments along the migration channel within the buffer;
a laser attached to the rear of the detecting means for illuminating the DNA fragments;
means for detecting fluorescent light emitted from the illumination fragments along the migration channel; and,
means for generating a full image of the separation apparatus and the separated DNA fragments.

17. The method of claim 6 wherein the buffer is a gel.

18. The method of claim 6 wherein the buffer is a polymer solution.

19. The method of claim 6 wherein the separation apparatus comprises a plurality of capillary tubes forming the migration channels.

20. The method of claim 6 wherein the separation apparatus comprises a set of glass plates with lithographically etched channels forming the migration channels.

21. The apparatus of claim 11 wherein the separation apparatus comprises:
at least on capillary tube;
a buffer; and,
a means for providing an electric field to create a bias between ends of the capillary tube.

22. The apparatus of claim 11 wherein the separation apparatus comprises:
a stacked pair of lithographically etched glass plates;
a buffer; and,
a means for providing an electric field to create a bias between ends of the glass plates.

23. The system of claim 16 wherein the detecting means comprises a full-width array scanner.

* * * * *